United States Patent [19]

Hellings et al.

[11] Patent Number: 5,620,843
[45] Date of Patent: Apr. 15, 1997

[54] NON-A NON-B SEQUENCES

[75] Inventors: Jan A. Hellings, Boxtel; Johannes J. Wilhelmus de Haard, Michielsgestel, both of Netherlands

[73] Assignee: Akzo Nobel N.V., Arnhem, Netherlands

[21] Appl. No.: 867,194

[22] PCT Filed: Jun. 14, 1991

[86] PCT No.: PCT/EP91/01110

§ 371 Date: Jun. 26, 1992

§ 102(e) Date: Jun. 26, 1992

[87] PCT Pub. No.: WO92/00328

PCT Pub. Date: Jan. 9, 1992

[30] Foreign Application Priority Data

Jun. 30, 1990 [EP] European Pat. Off. .............. 90201746

[51] Int. Cl.$^6$ ........................................................ C12Q 1/70
[52] U.S. Cl. .................. 435/5; 435/252.3; 435/320.1; 436/536; 530/388.3; 530/389.4
[58] Field of Search ............... 536/23.72; 530/388.1, 530/387.9, 324, 388.3, 389.4; 435/252.3, 320.1, 5, 6; 436/536

[56] References Cited

FOREIGN PATENT DOCUMENTS

| | | |
|---|---|---|
| 0293274 | 11/1988 | European Pat. Off. . |
| 0318216 | 5/1989 | European Pat. Off. . |
| 0363025 | 4/1990 | European Pat. Off. . |
| 0388232 | 9/1990 | European Pat. Off. . |
| 0398748 | 11/1990 | European Pat. Off. . |

OTHER PUBLICATIONS

The 1988/89 Promega Catalog, Chapter 12, p. 10.
K. Takeuchi et al., "Hepatitis C viral cDNA clones isolated from a healthy carrier donor implicated in post–transfusion non–A, non–B hepatitis," Gene, vol. 91, No. 2, pp. 287–291, Jul. 16, 1990, The Netherlands.
H. Okamoto et al., "The 5'–terminal sequence of the hepatitis C virus genome," Japan. J. Exp. Med., vol. 60, No. 3, pp. 166–177, 1990.
Y. Kubo et al., "A cDNA fragment of hepatitis C virus isolated from an implicated donor of post–transfusion non–A, non–B hepatitis in Japan," Nucleic Acid Research, vol. 17, No. 24, pp. 10367–10372, 1989.

*Primary Examiner*—W. Gary Jones
*Assistant Examiner*—Scott Houtteman
*Attorney, Agent, or Firm*—William M. Blackstone; Mary E. Gormley

[57] ABSTRACT

A peptide within a non-A non-B hepatitis virus genome reacts with antibodies found in individuals infected with non-A non-B hepatitis virus. The peptide is described along with the nucleic acid which encodes this peptide, antibodies directed against the peptide, as well as vectors, host cells and kits comprising these products. Also described are methods of detection of non-A non-B hepatitis using these products.

15 Claims, 2 Drawing Sheets

Figure 1

ATG-GTG-GGG-AAC-TGG-GCG-AAG-GTC-CTC-GTA-GTG-CTC-CTG-
CTA-TTC-GCC-GGC-GTC-GAC-GCG-GAA-ACC-CAC-GTC-ACC-GGG-
GGA-AAT-GTC-GCT-CGC-ACC-GCC-GCG-AGA-TTC-GCA-GGC-CTC-
TTC-ACA-CCG-GGT-GCC-CAG-CAG-AAC-GTC-CAG-CTG-ATC-GAC-
TCC-AAT-GGC-AGT-TGG-CAC-ATC-AAT-AGC-ACG-GCC-TTG-AAC-
TGT-AAT-GCC-AGC-CTC-GAC-ACC-GGC-TGG-CTA-GCA-GGG-CTC-
TTC-TAC-TAC-AAC-AAA-TTC-AAC-TCT-TCA

Figure 2

Met-Val-Gly-Asn-Trp-Ala-Lys-Val-Leu-Val-Val-Leu-Leu-
Leu-Phe-Ala-Gly-Val-Asp-Ala-Glu-Thr-His-Val-Thr-Gly-
Gly-Asn-Val-Ala-Arg-Thr-Ala-Ala-Arg-Phe-Ala-Gly-Leu-
Phe-Thr-Pro-Gly-Ala-Gln-Gln-Asn-Val-Gln-Leu-Ile-Asp-
Ser-Asn-Gly-Ser-Trp-His-Ile-Asn-Ser-Thr-Ala-Leu-Asn-
Cys-Asn-Ala-Ser-Leu-Asp-Thr-Gly-Trp-Leu-Ala-Gly-Leu-
Phe-Tyr-Tyr-Asn-Lys-Phe-Asn-Ser-Ser

NON-A NON-B SEQUENCES

This application is the national filing of PCT application No. PCT/EP91/01110.

The invention relates to a nucleic acid sequence coding for a peptide or a fragment thereof which is immunochemically reactive with NANBH virus antibodies (Non-A Non-B Hepatitis).

The invention also relates to a method for the detection of NANBH or anti-NANBH in a test fluid and also to an immunochemical reagent and a test kit for carrying out the said detection methods.

Non-A, Non-B hepatitis which may or may not be caused by Hepatitis C Virus (HCV) is a transmissible disease or family of diseases shown to be virus-induced. It can be distinguished from other forms of viral-associated liver diseases, including that caused by the known hepatitis viruses, i.e., hepatitis A virus (HAV), hepatitis B virus (HBV), and delta hepatitis virus (HDV), as well as the hepatitis induced by cytomegalovirus (CMV) or Epstein-Barr virus (EBV). NANBH was first identified in transfused individuals. Transmission from man to chimpanzee and serial passage in chimpanzees provided evidence that NANBH is due to a transmissible infectious agent or agents.

Epidemiologic evidence is suggestive that three types of NANBH exist: the water-borne epidemic type; the blood or needle associated type; and the sporadically occurring (community acquired) type. However, the number of agents which may be the causative of NANBH is unknown.

Clinical diagnosis and identification of NANBH has been accomplished primarily by exclusion of other viral markers. Among the methods used to detect putative NANBH antigens and antibodies are agar-gel diffusion, counter-immunoelectrophoresis, immunofluorescence microscopy, immune electron microscopy, radioimmunoassay, and enzyme-linked immunosorbent assay. However, none of these assays has proved to be sufficiently sensitive, specific, and reproducible to be used as a diagnostic test for NANBH.

However, for the development of a specific and sensitive method to enable a reliable diagnosis to be made in various phases of the infection with NANBH it is of great importance to identify immuno-dominant viral epitopes of this type.

A nucleic acid sequence according to FIG. 1 (SEQ. ID NO: 5) or a fragment thereof has now been found coding for a peptide which is surprisingly immunochemically reactive with NANBH-antibodies.

The invention further comprises a peptide with 87 amino acids and an amino acid sequence as shown in FIG. 2 which is immunochemically reactive with NANBH antibodies. Said amino acid sequence does not correspond to any published amino acid sequence with regard to NANBH (for example the published sequence of Chiron in EP 318,216).

The invention also comprises fragments of the said peptide which are still immunochemically reactive with NANBH-antibodies and also polypeptides comprising the said peptide or said fragment thereof.

The invention also relates to an immunochemical reagent, which reagent comprises at least one of the peptides or fragments thereof according to the invention.

The invention also comprises a method for the detection of antibodies directed against NANBH in a test fluid, using at least one of the peptides according to the invention.

The invention also relates to a method for the detection of NANBH in a test fluid, using at least one of the peptides according to the invention.

The invention also relates to a test kit to be used in an immuno-assay, said test kit containing at least an immunochemical reagent according to the invention.

It is within the scope of this invention to use the new nucleotide sequence according to FIG. 1 as the basis of a test to detect NANBH DNA or RNA by a nucleic acid amplification technique for instance the polymerase chain reaction (PCR) or the nucleic acid sequence based amplification (NASBA), as described in EP 201,184 and EP 329,822, respectively.

Moreover, a peptide or fragment thereof according to the invention can be used in suitable pharmaceutical dosage forms in the treatment of NANB Hepatitis-disease. The preparation of vaccines thus obtained which contain a peptide or fragment thereof as active ingredients, is known to one skilled in the art.

BRIEF DESCRIPTION OF THE DRAWINGS

FIG. 1. A region of a non-A non-B hepatitis virus genome coding for a peptide which is immunochemically reactive with antibodies found in individuals infected with the virus.

FIG. 2. The peptide encoded by the nucleic acid of FIG. 1.

The peptides mentioned above are found to be particularly suitable for use in a diagnostic method for the determination of the presence of NANBH or NANBH-antibodies in a test fluid.

In contrast to the natural NANBH, the peptides according to the invention have the great advantage that these are of a safe non-infectious origin.

The preparation of the peptides according to the invention is effected by means of one of the known organic chemical methods for peptide synthesis or with the aid of recombinant DNA techniques. This latter method involves the preparation of the desired peptide by means of bringing to expression a recombinant polynucleotide with a polynucleotide sequence which is coding for one or more of the peptides in question in a suitable micro-organism as host.

The organic chemical methods for peptide synthesis are considered to include the coupling of the required amino acids by means of a condensation reaction, either in homogeneous phase or with the aid of a so-called solid phase.

The condensation reaction can be carried out as follows:

a) condensation of a compound (amino acid, peptide) with a free carboxyl group and protected other reactive groups with a compound (amino acid, peptide) with a free amino group and protected other reactive groups, in the presence of a condensation agent, b) condensation of a compound (amino acid, peptide) with an activated carboxyl group and free or protected other reaction groups with a compound (amino acid, peptide) with a free amino group and free or protected other reactive groups.

Activation of the carboxyl group can take place, inter alia, by converting the carboxyl group to an acid halide, azide, anhydride, imidazolide or an activated ester, such as the N-hydroxy-succinimide, N-hydroxy-benzotriazole or p-nitrophenyl ester.

The most common methods for the above condensation reactions are: the carbodiimide method, the azide method, the mixed anhydride method and the method using activated esters, such as described in The Peptides, Analysis, Synthesis, Biology Vol. 1–3 (Ed. Gross, E. and Meienhofer, J.) 1979, 1980, 1981 (Academic Press, Inc.).

Preparation of suitable fragments of abovementioned peptides according to the invention using the "solid phase" is for instance described in J. Amer. Chem. Soc. 85, 2149 (1963) and Int. J. Peptide Protein Res. 35, 161–214 (1990). The coupling of the amino acids of the peptide to be prepared usually starts from the carboxyl end side. For this method a solid phase is needed on which there are reactive groups or on which such groups can be introduced. This can be, for example, a copolymer of benzene and divinylbenzene with reactive chloromethyl groups, or a polymeric solid phase rendered reactive with hydroxymethyl or amine-function.

A particularly suitable solid phase is, for example, the p-alkoxybenzyl alcohol resin (4-hydroxy-methyl-phenoxymethyl-copolystrene-1% divinylbenzene resin), described by Wang (1974) J. Am. Chem. Soc. 95, 1328. After synthesis the peptides can be split from this solid phase under mild conditions.

After synthesis of the desired amino acid sequence, detaching of the peptide from the resin follows, for example, with trifluoromethanesulphonic acid or with methanesulphonic acid dissolved in trifluoroacetic acid. The peptide can also be removed from the carrier by transesterification with a lower alcohol, preferably methanol or ethanol, in which case a lower alkyl ester of the peptide is formed directly. Likewise, splitting with the aid of ammonia gives the amide of a peptide according to the invention.

The reactive groups which may not participate in the condensation reaction are, as stated, effectively protected by groups which can be removed again very easily by hydrolysis with the aid of acid, base or reduction. Thus, a carboxyl group can be effectively protected by, for example, esterification with methanol, ethanol, tertiary butanol, benzyl alcohol or p-nitrobenzyl alcohol and amines linked to solid support.

Groups which can effectively protect an amino group are the ethoxycarbonyl, benzyloxycarbonyl, t-butoxy-carbonyl or p-methoxy-benzyloxycarbonyl group, or an acid group derived from a sulphonic acid, such as the benzene-sulphonyl or p-toluene-sulphonyl group, but other groups can also be used, such as substituted or unsubstituted aryl or aralkyl groups, for example benzyl and triphenylmethyl, or groups such as ortho-nitrophenyl-sulphenyl and 2-benzoyl-1-methylvinyl. A particularly suitable α-amino-protective group is, for example, the base-sensitive 9-fluorenylmethoxycarbonyl (Fmoc) group [Carpino & Han (1970) J. Amer. Chem. Soc. 92, 5748].

A more extensive account of possible protecting groups can be found in The Peptides, Analysis, Synthesis, Biology, Vol. 1–9 (Eds. Gross, Udenfriend and Meienhofer) 1979–1987 (Academic Press, Inc.).

It is necessary also to protect the ε-amino group of lysine and advisable for the guanidine group of arginine. Customary protective groups in this connection are a Boc-group for lysine and a Pmc- or Pms- or Mbs-group or Mtr-group for arginine.

The protective groups can be split off by various conventional methods, depending on the nature of the particular group, for example with the aid of trifluoroacetic acid or by mild reduction, for example with hydrogen and a catalyst, such as palladium, or with HBr in glacial acetic acid.

As already indicated above, the peptide according to the invention can likewise be prepared with the aid of recombinant DNA techniques. This possibility is of importance particularly when the peptide is incorporated in a repeating sequence ("in tandem") or when the peptide can be prepared as a constituent of a (much larger) protein or polypeptide. This type of preparation of the peptide therefore likewise falls within the scope of the invention. For this purpose, as a constituent of a recombinant DNA, a polynucleotide is used which codes for the peptide according to the invention and which, furthermore, is substantially free from polynucleotide segments, which in the naturally occurring NANBH genome flank the polynucleotide sequence indicated above.

A polynucleotide of this type, which is coding for the peptide according to the invention, and a recombinant DNA in which this polynucleotide is incorporated likewise fall within the scope of the invention.

Without specifically being incorporated in the claims, it is self-evident that one or more amino acids in the peptides according to the invention can be replaced by other aminoacids or amino acid analogues or derivatives without affecting the immunochemical activity of the peptides in question.

In addition the functional derivatives of these peptides, by which are meant in the main:

(a) acid addition salts of the peptides;

(b) amides of the peptides and specifically the C-terminal amides;

(c) esters and specifically C-terminal esters and (d) N-acyl derivatives, specifically N-terminal acyl derivatives and in particular N-acetyl derivatives, are also considered as peptides according to the invention.

The peptides or fragments thereof prepared and described above are used to produce antibodies, both polyclonal and monoclonal. Monoclonal antibodies directed against peptides according to the invention can be readily produced by one skilled in the art. Making monoclonals by hybridomas is well known. By cell fusion immortal antibody-producing cell lines can be created while also other techniques are available such as direct transformation of B-lymphocytes with oncogenic DNA or transfection with Epstein-Barr Virus. Antibodies, both monoclonal and polyclonal, directed against peptides according to the invention are very suitable in diagnosis, while those antibodies which are neutralizing are very useful in passive immunotherapy. Especially monoclonal antibodies may be used to raise anti-idiotype antibodies. Techniques for raising anti-idiotype antibodies are known in the art. Said anti-idiotype antibodies are also useful for treatment of NANBH, as well as for the elucidation of important epitopic regions of NANBH-antigens.

The term "immunochemical reagent" according to the invention usually consists of one more peptides according to the invention and a suitable support or a labelling substance.

Supports which can be used are, for example, the inner wall of a microtest well or a cuvette, a tube or capillary, a membrane, filter, test strip or the surface of a particle such as, for example, a latex particle, an erythrocyte, a dye sol, a metal sol or metal compound as sol particle, a carrier protein such as BSA or KLH.

Labelling substances which can be used are, inter alia, a radioactive isotope, a fluorescent compound, an enzyme, a dye sol, metal sol or metal compound as sol particle.

In a method for the detection of antibodies directed against NANBH in a test fluid, an immunochemical reagent according to the invention is brought into contact with the test fluid. After which, the presence of immune complexes formed between the peptide and antibodies in the test fluid is detected and by this detection the presence of NANBH antibodies in the test fluid is known and can be determined quantitatively.

Depending on the nature and further characteristics of the immunochemical reagent the immunochemical reaction that takes place is a so called sandwich reaction, an agglutination reaction, a competition reaction or an inhibition reaction.

For the detection of NANBH in a test fluid an immunochemical reagent according to the invention is brought into contact with the test fluid and anti-NANBH after which the presence of immune complexes formed is detected and, from this, the presence of NANBH in a test fluid can be determined.

A particularly suitable method for the detection of NANBH in a test fluid is based on a competition reaction between a peptide according to the invention provided with a labelling substance and a NANBH antigen (present in the test fluid) whereby the peptide and the antigen are competing with the antibody directed against NANBH attached to a solid support.

A test kit according to the invention comprises as an essential constituent an immunochemical reagent as described above. Carrying out a sandwich reaction, for the detection of NANBH antibodies the test kit may comprise, for example, the peptide according to the invention coated to a solid support, for example the inner wall of a microtest well, and either a labelled peptide according to the invention or a labelled anti-antibody.

For carrying out a competition reaction, the test kit may comprise a peptide according to the invention coated to a solid support, and a labelled antibody directed against NANBH preferably a monoclonal antibody directed against said peptide.

In an agglutination reaction the test kit comprises an immunochemical reagent which may comprise a peptide according to the invention coated to particles or sols.

Another embodiment of a test kit is, for example, the use of a labelled peptide according to the invention as immunochemical reagent in a competition reaction with a NANBH antigen to be detected for a binding site on the antibody directed against NANBH, which is coated to a solid support.

EXAMPLE 1

Procedure for isolating the clones (for isolating new sequences of the NANB-hepatitis virus)

RNA was isolated from serum of chimpanzees in the chronic phase of NANB hepatitis. Serum was diluted by adding two volumes of SST-buffer (10 mM Tris-HCl, pH 7.6), and pelleted for two hours at 300.000 g. The pellet was dissolved in 1/10 volume of SST-buffer and centrifuged through a sucrose-gardient of 5–20% sucrose in SST-buffer at 200.000 g for three hours.

The pelleted material was dissolved in TE buffer (1/100 of the original serum volume) and treated with proteinase K. The RNA was isolated by standard techniques (phenol, phenol/chloroform, chloroform extractions) and precipitated by ethanol.

RNA was solved in aqua-bidest and treated by DNA'se in 10 mM $MgCl_2$ to remove contaminating DNA and the RNA was reextracted and reprecipitated. The quality and quantity of the RNA-preparation was checked by $^{32}P$-nucleotide polyA-addition and DNA labelling together with appropriate standards.

The RNA was reverse-transcribed using standard techniques with a twenty-four nucleotides long primer complementary to the DNA sequence as given in the Chiron-patent application EP 318,216 (nucleotides nrs. 60 till 83,=primer 637), extended with an EcoRI-site at its 5'-end. This primer was synthesized on an Applied Biosystems DNA synthesizer. The c-DNA was isolated and elongated by the addition of polyG to the 3'-end. The second c-DNA strand was synthesized using as primer the sequence 5'-GGAATT(C) 13 (complementary to the polyG-tail, with an added EcoRI-site in order to enable later cloning steps). The cDNA was amplified with as primers the GGAATT(C) 13 primer mentioned above and the twenty-four nucleotides primer mentioned above. The amplified DNA was cut with the restriction-enzyme EcoRI and ligated into the lambda gt10 vector. The DNA coding for the extension was immediately amplified using as primers either the lambda gt10 forward or reverse primer (as provided by New England Biolabs) together with the primer complementary to nucleotide nrs. 6 till 35 of the "Chiron"-sequence (primer 638).

The amplified DNA was directly cloned into the EcoRI-Sma-I sites of the vector pGEM-4 (Promega). Clones posessing an insert were detected by amplification using as primers 638 and M13 forward (New England Biolabs). The longest insert contained the sequence:
ACCGGCTGGCTAGCAGGGCTCTTCTAC-TACAACAAATTCAACTCTT (named Ex-1)(SEQ. ID NO:1)

In a second round the sequence TAGTAGAAGAGCCCT-GCTAG (primer 008), (SEQ. ID. NO: 2) complementary to nucleotide 10 to 20 of the sequence described above, was used, after digestion with EcoRI and phosphorylation, as a primer together with the lambda gt-10 forward and reverse primers, described above, to amplify sequences from the lambda gt-10 ligation mix described above, which extend from the 5'-end of the sequence Ex-1 described above. The amplified DNA was directly cloned into the vector pGEM-7-f (Promega). Clones posessing an insert were detected by amplification using as primers 008 (described above) and M13 forward (New England Biolabs). Sequencing of the longest insert revealed the sequence:

ATGGTGGGGAACTGGGCGAAGGTCCTCGTAGTGCTCCTGCTATTCGCCGGCGTC

GACGCGGAAACCCACGTCACCGGGGGAAATGTCGCTCGCACCGCCGCGAGATTC

GCAGGCCTCTTCACACCGGGTGCCCAGCAGAACGTCCAGCTGATCGACTCCAAT

GGCAGTTGGCACATCAATAGCACGGCCTTGAACTGTAATGCCAGCCTCGAC-3' (named Ex-2), (SEQ ID NO: 3).

The complete sequence therefore contains the following nucleotides from 5' to 3'-end:

ATGGTGGGGAACTGGGCGAAGGTCCTCGTAGTGCTCCTGCTATTCGCCGGCGTC

GACGCGGAAACCCACGTCACCGGGGGAAATGTCGCTCGCACCGCCGCGAGATTC

-continued

GCAGGCCTCTTCACACCGGGTGCCCAGCAGAACGTCCAGCTGATCGACTCCAAT

GGCAGTTGGCACATCAATAGCACGGCCTTGAACTGTAATGCCAGCCTCGACACC

GGCTGGCTAGCAGGGCTCTTCTACTACAACAAATTCAACTCTT, (SEQ ID NO: 4).

This sequence was cloned in the expression vector pMBL1113 in the correct reading frame within the beta-galactosidase coding gene. For this purpose from the c-DNA described the complete sequence was amplified using as primers sequences identical respectively complementary to the 20 nucleotides on the extreme ends with BamH1 resp. HindIII-sites added to their 5'-end to enable cloning in the correct reading frame of the lac-Z gene in the expression vector. The expression of the hybrid beta-galactosidase was induced by 10 mM IPTG using standard procedures in a 1.5 ml culture. The cells were pelleted by centrifugation and solved in ⅕th of the original volume in SDS-PAGE buffer. Immediately after resuspending the pellet and boiling the suspension for 10 minutes, 3 µl of the suspension was loaded on a SDS-PAGE-gel and after electrophoresis, blotted to nitrocellulose filter by electroelution. These blots were incubated with the NANBH-sera under investigation after blocking the filters with skimmed milk using standard procedures. The blots were developed by detecting immune-complexes with HRP-conjugated mouse anti-human-IgG (Promega) using the procedure recommended by the supplier.

This same sequence was transferred to the baculovirus transfer vector behind the p-10 promotor using the BamH-1 sites of the pMBL1113 hybrid. Recombinant baculovirus, expressing the sequence described above was obtained using standard procedures. This expression product was tested with NANBH-sera using essentially the same procedures as described for the *E. coli* system.

Sequencing of the expression vectors revealed the sequence as expected.

EXAMPLE II

Overlapping peptides (10–15 amino acids in length) according to the sequences of FIG. 2 (SEQ. ID. NO: 6) were prepared and dissolved to 7.5 µg/ml in 100 mM phosphate buffer pH 8.0. Microtiter plates were pretreated with 0.2% glutaraldehyde in phosphate buffer pH 5.0 at 135 µl per well for 4 h at room temperature under continuous shaking. Plates were then emptied and 135 µl of the above peptide solution was given to each well. Binding of the peptide to the microtiter plate was allowed to proceed for 3 h at 37° C. The plates were frozen and stored overnight at −20° C.

Subsequently the plates were thawed and emptied, and residual binding sites were blocked with a solution of 0.05% Tween 20® in 0.2M Tris pH 7.4/0.2M NaCl for 5 min. at room temperature. Plates were then washed once with 0.2M Tris pH 7.4/0.2M NaCl and twice with 0.04M Tris pH 7.4, at 250 µl per well. For the determination of antibodies specific for Non-A Non-B hepatitis, the serum sample was diluted in sample diluent (phosphate buffered saline (PBS)/20% normal goat serum/1% Triton X100) pipetted into the well (100 µl per well) and incubated for 1 h at 37° C. After washing the wells with PBS/0.05% Tween 20® the bound human antibodies were detected with goat anti-human immunoglobulin labeled with peroxidase (100 µl per well, 1 h at 37° C.) diluted in sample diluent. The plates were washed 4 times with PBS/0.05% Tween 20®. TMB was added (100 µl per well) as a substrate for the peroxidase enzyme and the reaction was allowed to proceed for 30 min. at room temperature. The reaction was stopped by adding 100 µl 2M $H_2SO_4$ to each well. The yellow color was read at 450 nm in an Organon Teknika microelisa reader.

Using above-mentioned procedure it was established that epitopes recognised by human NANBH-sera are present on said sequences.

We claim:

1. A nucleic acid molecule comprising a nucleic acid sequence that codes for a non-A non-B hepatitis virus peptide with the amino acid sequence of SEQ ID NO:6 or tandem repeats of SEQ ID NO: 6, wherein the nucleic acid molecule is free from polynucleotide segments which in the naturally occurring non-A non-B hepatitis genome flank the nucleic acid sequence that codes for said peptide.

2. The nucleic acid molecule according to claim 1, which comprises the nucleic acid sequence depicted in SEQ ID NO:5.

3. A non-A non-B hepatitis virus peptide comprising the amino acid sequence depicted in SEQ ID NO:6, wherein the peptide is substantially free from peptide segments which, in the naturally occurring non-A non-B hepatitis virus polypeptides, flank said peptide with the amino acid sequence of SEQ ID NO:6.

4. An immunochemical reagent comprising a peptide according to claim 3.

5. A vector comprising a nucleic acid molecule as defined in claim 1.

6. A host cell comprising a nucleic acid molecule as defined in claim 1.

7. A host cell comprising a vector as defined in claim 5.

8. An antibody directed against an epitope found in the peptide according to claim 3.

9. The antibody of claim 8, which is a monoclonal antibody.

10. A method for the detection of antibodies directed against non-A non-B hepatitis virus in a test fluid, comprising contacting an immunochemical reagent according to claim 4 with a test fluid, and detecting the presence of immune complexes formed between the peptide of the immunochemical reagent and antibodies in the test fluid, which is a measure for the presence of non-A non-B hepatitis antibodies in the test fluid.

11. A method for the detection of non-A non-B hepatitis in a test fluid, comprising contacting an immunochemical reagent according to claim 4 with the test fluid and anti-non-A non-B hepatitis antibodies and detecting the presence of immune complexes formed, thereby determining the presence of non-A non-B hepatitis in the test fluid.

12. A method for the amplification and the detection of a non-A non-B hepatitis nucleic acid molecule in a test fluid, comprising:

contacting the molecule of claim 14 and the test fluid under conditions such that the claim 14 molecule will be a primer for a nucleic acid amplification reaction, performing the nucleic acid amplification reaction, detecting the presence of an amplification product, wherein the presence of an amplification product is indicative of the presence of a non-A non-B hepatitis nucleic acid molecule in the test fluid.

13. A test kit for performing an immunoassay comprising an immunochemical reagent according to claim 4 bound to a support and packaged.

14. A test amplification kit for performing an amplification method to detect non-A non-B hepatitis comprising a molecule according to claim 14 as a primer that is packaged.

15. A host cell comprising a vector according to claim 5.

* * * * *

UNITED STATES PATENT AND TRADEMARK OFFICE
CERTIFICATE OF CORRECTION

PATENT NO. : 5,620,843
DATED : April 15, 1997
INVENTOR(S) : Hellings et al.

It is certified that error appears in the above-indentified patent and that said Letters Patent is hereby corrected as shown below:

claim 14, column 12, line 3, by deleting "14" and replacing with -- 1 --.

Signed and Sealed this

Fourteenth Day of October, 1997

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: unknown ( i i ) MOLECULE TYPE: cDNA ( x i ) SEQUENCE DESCRIPTION: SEQ ID NO:1:

ACCGGCTGGC    TAGCAGGGCT    CTTCTACTAC    AACAAATTCA    ACTCTT    46

( 2 ) INFORMATION FOR SEQ ID NO:2:

( i ) SEQUENCE CHARACTERISTICS:

( A ) LENGTH: 20 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:2:

TAGTAGAAGA GCCCTGCTAG                                                                              20

( 2 ) INFORMATION FOR SEQ ID NO:3:

( i ) SEQUENCE CHARACTERISTICS:
( A ) LENGTH: 213 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:3:

ATGGTGGGGA ACTGGGCGAA GGTCCTCGTA GTGCTCCTGC TATTCGCCGG CGTCGACGCG    60
GAAACCCACG TCACCGGGGG AAATGTCGCT CGCACCGCCG CGAGATTCGC AGGCCTCTTC   120
ACACCGGGTG CCCAGCAGAA CGTCCAGCTG ATCGACTCCA ATGGCAGTTG GCACATCAAT   180
AGCACGGCCT TGAACTGTAA TGCCAGCCTC GAC                                213

( 2 ) INFORMATION FOR SEQ ID NO:4:

( i ) SEQUENCE CHARACTERISTICS:
( A ) LENGTH: 259 base pairs
( B ) TYPE: nucleic acid
( C ) STRANDEDNESS: both
( D ) TOPOLOGY: unknown ( i i ) MOLECULE TYPE: cDNA ( x i ) SEQUENCE DESCRIPTION: SEQ ID NO:4:

ATGGTGGGGA ACTGGGCGAA GGTCCTCGTA GTGCTCCTGC TATTCGCCGG CGTCGACGCG    60
GAAACCCACG TCACCGGGGG AAATGTCGCT CGCACCGCCG CGAGATTCGC AGGCCTCTTC   120
ACACCGGGTG CCCAGCAGAA CGTCCAGCTG ATCGACTCCA ATGGCAGTTG GCACATCAAT   180
AGCACGGCCT TGAACTGTAA TGCCAGCCTC GACACCGGCT GGCTAGCAGG GCTCTTCTAC   240
TACAACAAAT TCAACTCTT                                                259

( 2 ) INFORMATION FOR SEQ ID NO:5:

( i ) SEQUENCE CHARACTERISTICS:
( A ) LENGTH: 261 base pairs
( B ) TYPE: nucleic acid
( C ) STRANDEDNESS: both
( D ) TOPOLOGY: both ( i i ) MOLECULE TYPE: cDNA ( x i ) SEQUENCE DESCRIPTION: SEQ ID NO:5:

ATGGTGGGGA ACTGGGCGAA GGTCCTCGTA GTGCTCCTGC TATTCGCCGG CGTCGACGCG    60
GAAACCCACG TCACCGGGGG AAATGTCGCT CGCACCGCCG CGAGATTCGC AGGCCTCTTC   120
ACACCGGGTG CCCAGCAGAA CGTCCAGCTG ATCGACTCCA ATGGCAGTTG GCACATCAAT   180
AGCACGGCCT TGAACTGTAA TGCCAGCCTC GACACCGGCT GGCTAGCAGG GCTCTTCTAC   240
TACAACAAAT TCAACTCTTC A                                             261

( 2 ) INFORMATION FOR SEQ ID NO:6:

( i ) SEQUENCE CHARACTERISTICS:
    ( A ) LENGTH: 87 amino acids
    ( B ) TYPE: amino acid
    ( C ) STRANDEDNESS: single
    ( D ) TOPOLOGY: unknown ( i i ) MOLECULE TYPE: peptide ( x i ) SEQUENCE DESCRIPTION: SEQ ID NO:6:

```
Met Val Gly Asn Trp Ala Lys Val Leu Val Val Leu Leu Leu Phe Ala
 1           5                  10                  15
Gly Val Asp Ala Glu Thr His Val Thr Gly Gly Asn Val Ala Arg Thr
            20                  25                  30
Ala Ala Arg Phe Ala Gly Leu Phe Thr Pro Gly Ala Gln Gln Asn Val
        35              40                  45
Gln Leu Ile Asp Ser Asn Gly Ser Trp His Ile Asn Ser Thr Ala Leu
    50              55                  60
Asn Cys Asn Ala Ser Leu Asp Thr Gly Trp Leu Ala Gly Leu Phe Tyr
65              70                  75              80
Tyr Asn Lys Phe Asn Ser Ser
            85
```